United States Patent [19]

Hetland

[11] Patent Number: 4,816,032
[45] Date of Patent: Mar. 28, 1989

[54] ARRANGEMENT IN AN INTRAOCULAR ANTERIOR CHAMBER LENS

[76] Inventor: Jens G. Hetland, Trosteveien 16, Bekkestua, Norway, 1340

[21] Appl. No.: 154,894

[22] Filed: Feb. 11, 1988

[30] Foreign Application Priority Data

Feb. 11, 1987 [NO] Norway .................................. 870532

[51] Int. Cl.$^4$ ............................................... A61F 2/16
[52] U.S. Cl. ................................................ 623/6
[58] Field of Search ........................................... 623/4-6

[56] References Cited

U.S. PATENT DOCUMENTS

| | | | |
|---|---|---|---|
| 4,192,022 | 3/1980 | LaHaye | 623/6 |
| 4,418,431 | 12/1983 | Feaster | 623/6 |
| 4,466,705 | 8/1984 | Michelson | 623/6 X |
| 4,503,570 | 3/1985 | Grendahl | 623/6 |
| 4,605,410 | 8/1986 | Grendahl | 623/6 |
| 4,624,669 | 11/1986 | Grendahl | 623/5 |

FOREIGN PATENT DOCUMENTS 0067765 12/1982 European Pat. Off. ................ 623/6

Primary Examiner—Ronald L. Frinks
Attorney, Agent, or Firm—Darby & Darby

[57] ABSTRACT

An artificial intraocular lens intended to be operated into the anterior chamber of the eye. The lens comprises an optical portion, and a haptic portion. A pressure equalizing aperture is provided so closely to the optical center of the optical portion that the pressure equalizing aperture will cause pressure equalization between the anterior chamber and the posterior chamber of the eye without use of iridectomy, thus preventing glaucoma from developing due to the fact that iris lies in contact with the optical portion.

3 Claims, 2 Drawing Sheets

ARRANGEMENT IN AN INTRAOCULAR ANTERIOR CHAMBER LENS

The present invention relates to an arrangement in an artifiical intraocular anterior chamber lens, below called IOL, intended for being operated into the anterior chamber of the eye. The lens comprises an optical portion, and loops (haptic portion). The lens may be manufactured from acrylic material (PMMA) or another suitable material.

Such artificial eye lenses may be used as an optical replacement of the natural lens when the latter has to be removed due to dimming phenomena reducing sight (cataract).

Today, a number of different variants of artificial anterior chamber lenses is known. Common to all of them is that it is necessary to operate a small hole iris (iridectomy) to prevent a pressure blocking between the anterior and posterior chambers of the eye. There is a constant production of liquid peripherally in the posterior chamber of the eye. The liquid flow goes through the posterior chamber forwards, through the pupil, and then leaves the eye peripherally in the anterior chamber corner of the eye. The pupil dilates in the dark and contracts under the influence of light. Also, the pupil gets smaller with advanced years. It is not uncommon that the pupil gets smaller than 2 mm in diameter. During treatment against glaucoma with eye drops the pupil may contract to 1 mm diameter. Also, the pupil gets small under influence of various medicaments (i.a. morphia) and it is small when we are asleep.

Under normal conditions the peripheral apertures which are provided in anterior chamber lenses of known kinds become blocked by iris and can, thus, not serve as pressure equalizing apertures between the anterior and posterior chambers.

If iridectomy is, thus, not performed, the pupil may, in certain situations, lie closely adjacent said IOL. This will cause an increase of pressure in the posterior chamber forcing iris and IOL forwards, so that the anterior chamber becomes shallow. The chamber corner is closed, and liquid cannot leave the eye through the natural discharge channels. The liquid pressure in the eye may, thus, build up to great heights. This is a very dangerous condition to the eye as it may result in glaucoma.

An iridectomy ensures that there will always be pressure equalization between the posterior and anterior chambers, and glaucoma will, thus, commonly not occur.

A disadvantage of iridectomy is that sometimes haemorrhage occurs during the operation. Furthermore, it is necessary to operate on a tissue rich in nerves and pigment. The hazard of haemorrhage is greatest with patients suffering from diabetes and glaucoma. An injury to the pigment may result in troublesome eyesight reflexes. Also, an opening in iris is unfortunate in the case of a rotation of IOL, since one loop of IOL might enter such an opening.

For an iridectomy to be carried out, the pupil should be small. It is, thus, necessary to administer additional medicaments (Acetylcholin), and it is known that such medicaments may cause various undesirable effects.

There are, on the whole, many arguments indicating that more advantages would be gained if iris is preserved intact. According to the invention it is proposed to place a pressure equalizing aperture through the optical portion so close to the center of the optical portion that the pressure equalizing aperture will cause pressure equalization between the anterior and posterior chambers of the eye independently of the size of the pupil.

The aperture is placed in such a manner that even if the pupil contracts very much, portions of the aperture will always stay open and permit free communication of liquid between the anterior and posterior chambers.

Further characterizing features will appear from the following claims and from the disclosure below.

The invention will be disclosed in more detail below with reference to the accompanying drawing.

Assumedly, mounting an artificial intraocular anterior chamber lens (IOL) in the anterior chamber of an eye is a generally known technique to those skilled in the art. An IOL 1 comprises a lens body 2, and at least two loops 3,4. Even though an IOL with two loops is shown, there are known IOL means for the anterior chamber of the eye provided with e.g. four loops.

Figure 1:
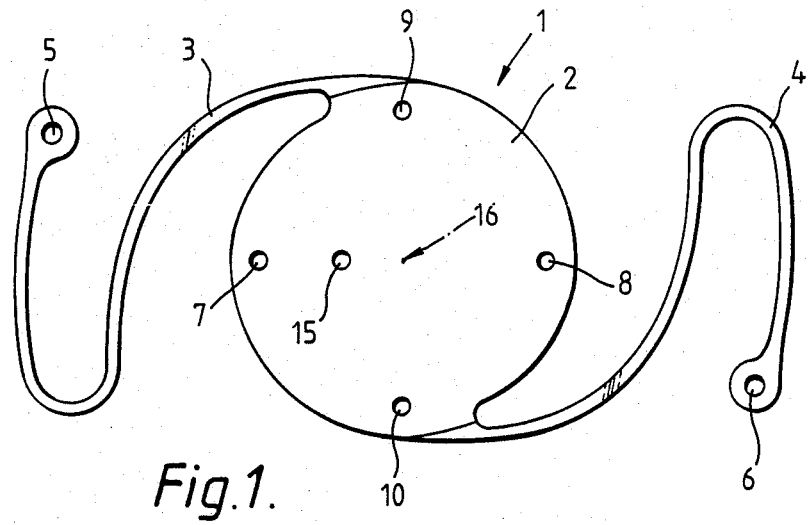
FIG. 1 shows an artificial intraocular anterior chamber lens in a plan view and at a much enlarged scale.
Figure 2:
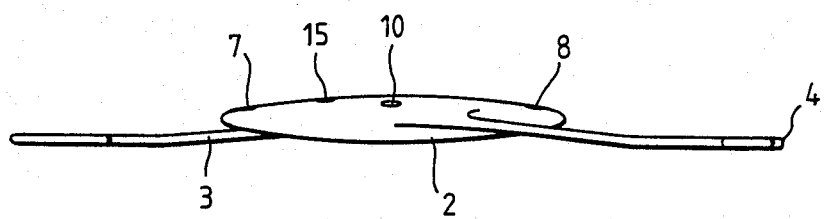
FIG. 2 shows the lens of FIG. 1 at the same scale in a vertical view.

It may be suitable to provide one or a plurality of positioning apertures, indicated in FIG. 1 by reference numerals 7, 8, 9, and 10, respectively. These apertures 7, 8, 9, and 10 are, thus, as will be obvious from FIG. 1, provided in a manner known per se along the periphery of the optical portion 2 of the lens. The apertures are designed for positioning IOL 1 in the anterior chamber of the eye as desired by the surgeon. It should be pointed out, especially, that these apertures are not pressure equalizing apertures, because the pupil may contract so much that they are covered by iris, as clearly appearing from FIG. 4. For some types of IOL lenses such apertures 7, 8, 9, 10 are not present, in which case the surgeon will use the loops in order to properly position the IOL lens.

Figure 4:
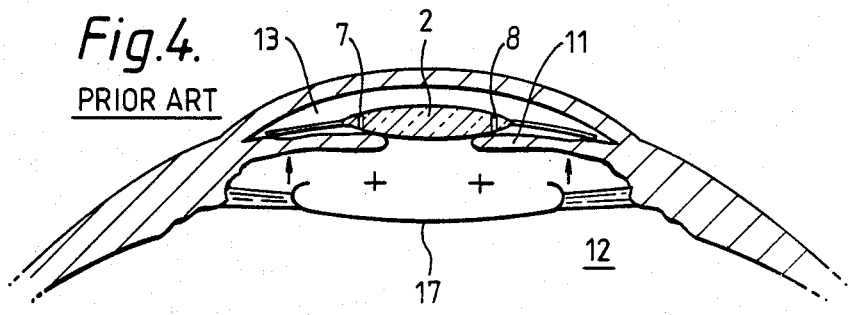
FIG. 4 illustrates an IOL mounted in the anterior chamber of an eye without any iridectomy.

It is obvious that without iridectomy iris 11 may in certain situations lie close to the optical portion 2 of said IOL. This will cause a rise of pressure in the posterior chamber 12 causing iris and said IOL to be forced forwards, as shown in FIG. 4, and also causing the anterior chamber 13 to become shallow. The most serious conditions in connection with this phenomenon is, however, that the patient may develop glaucoma because the liquid pressure in the eye gets far too high.

Figure 3:
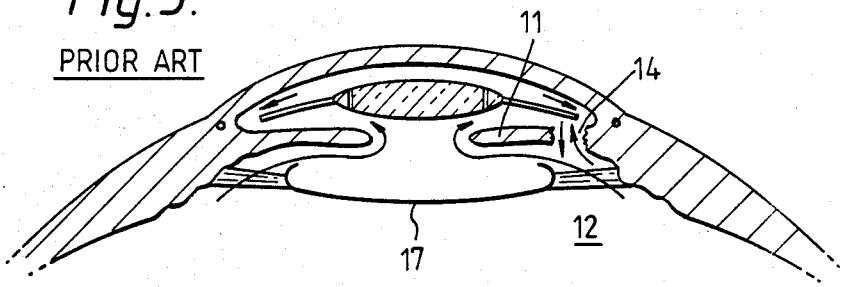
FIG. 3 illustrates an IOL mounted in the anterior chamber of an eye with iridectomy carried out.

As mentioned above, it is possible to avoid such an undesirable increase of pressure in connection with the known IOL by making an iridectomy, i.e. form a pressure equalizing hole 14 in iris 11 of the eye, see FIG. 3. Pressure will thus be equalized in the anterior and posterior chambers of the eye. Such iridectomy is, however, undesirable even though iridectomy may be helpful in a condition that may develop as shown in FIG. 4.

Figure 5:
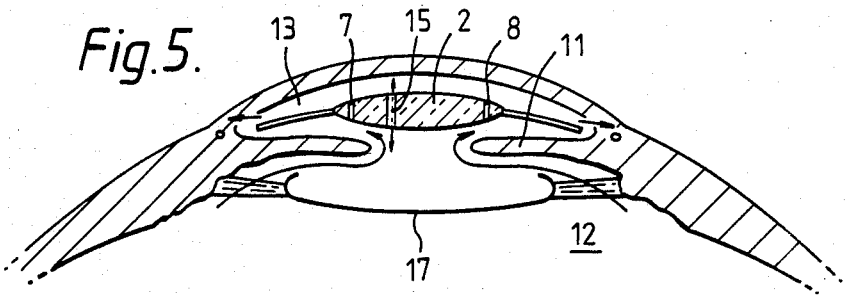
FIG. 5 illustrates an IOL according to the invention, which is mounted in the anterior chamber of an eye without any iridectomy.

As shown in FIG. 1, another aperture 15 serving as a pressure equalizing aperture is provided through the optical portion 2 of lens 1, and aperture 15 is preferably placed close to the optical center 16 of said optical portion 2. Said pressure equalizing aperture 15 is, thus, preferably placed closer to the center 6 of the optical portion than to the periphery of said optical portion. The aperture is placed in such a manner that portions of the aperture will always stay open and permit communication of liquid between the anterior and posterior chambers of the eye even when the pupil contracts strongly. Optical disadvantages of such a para-central pressure equalizing aperture 15 are not expected since the index of refraction of the liquid in the chambers of the eye and that of the material of the intraocular lens do not differ essentially. As will appear from FIGS. 3, 4, and 5, the natural lens of the eye has been removed with only the usual residue of the lens bag 17 of the lens remaining in a manner known per se.

Having thus described the invention, what is claimed is:

1. In an arrangement in an artificial intraocular lens intended for being operated into the anterior chamber of the eye, which lens comprises an optical portion, and loops (a haptic portion) the improvement comprising that a pressure equalizing aperture is provided through the optical portion so closely to the optical center of the optical portion that the pressure equalizing aperture will cause pressure equalization between the anterior and posterior chambers of the eye independently of the size of the pupil.

2. An arrangement as defined in claim 1,
   wherein said pressure equalizing aperture is placed at a shorter distance from said optical center than from the periphery of the optical portion, preferably within a distance from the optical center of 1/6 of the diameter of the optical portion.

3. An arrangement as defined in claim 1,
   wherein the intraocular lens is manufactured from a material having a natural index of refraction which is essentially equal to the normal index of refraction of the chamber liquid of the eye.

* * * * *